United States Patent [19]
Simpson

[11] 3,941,797
[45] Mar. 2, 1976

[54] 4-(HYDROXY-SUBSTITUTED-AMINO)-FURO[3,2-C]PYRIDINES

[75] Inventor: William R. Simpson, Mendham, N.J.

[73] Assignee: Sandoz, Inc., E. Hanover, N.J.

[22] Filed: July 26, 1974

[21] Appl. No.: 492,063

Related U.S. Application Data

[62] Division of Ser. No. 296,442, Oct. 10, 1972, Pat. No. 3,853,877.

[52] U.S. Cl. ............................ 260/296 H; 424/256
[51] Int. Cl.² ........................................ C07D 405/04
[58] Field of Search ...................... 260/297 B, 296 H

[56] References Cited
UNITED STATES PATENTS

| | | | |
|---|---|---|---|
| 3,637,700 | 1/1972 | Gabel et al. | 260/256.5 R |
| 3,853,877 | 12/1974 | Simpson | 260/268 FT |

OTHER PUBLICATIONS

Bourzat et al. *Bull. Soc. Chim. de France*, 1971, No. 5, pp. 1727–1730.

*Primary Examiner*—Paul M. Coughlan, Jr.
*Attorney, Agent, or Firm*—Gerald D. Sharkin; Richard E. Villa

[57] ABSTRACT

Disclosed are compounds of the class of furo[3,2-c]pyridines substituted at the 4-position by an amino function bearing a hydroxy-alkyl nitrate moiety, e.g., 4-[4-(2-hydroxyethyl)-1-piperazino]-furo[3,2-c]pyridine nitrate. The compounds have pharmacological activity in animals and are useful, for example, as anti-anginal agents. Also disclosed are the corresponding hydroxy intermediates which are useful in preparation of the nitrates and also as anti-anginal agents or as agents in the treatment of shock.

12 Claims, No Drawings

4-(HYDROXY-SUBSTITUTED-AMINO)-FURO[3,2-C]PYRIDINES

This is a division of application Ser. No. 296,442 filed Oct. 10, 1972, now U.S. Pat. No. 3,853,877.

This invention relates to furo[3,2-c]pyridine derivatives, and more particularly to furo[3,2-c]pyridines which are substituted at the 4- position by an amino function bearing a hydroxyalkyl nitrate moiety. The invention also relates to pharmaceutical methods and compositions utilizing said compounds. The invention further relates to the corresponding hydroxyalkyl substituted furo[3,2-c]pyridines useful as intermediates in preparation of said nitrates and also useful per se as pharmaceutically active substances.

The compounds of this invention may be represented by the strucutral formula I:

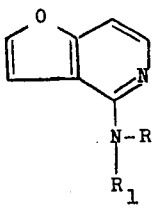
I wherein
R is from the group of
a. —CH$_2$(—CH$_2$)$_n$—ONO$_2$ b) —CH$_2$(—ĊH)$_n$—ONO$_2$, with R° substituent C) —ĊH(—CH$_2$)$_n$—ONO$_2$ with R' substituent d. —CH$_2$(—CH$_2$)$_z$—N[—CH$_2$(CH$_2$)$_y$—ONO$_2$]$_2$ R$_1$ is from the group of
e. —CH$_2$(—CH$_2$)n—ONO$_2$ when R is (a) as above defined,
f. hydrogen or lower alkyl of 1 to 4 carbon atoms, and R' is —(CH$_2$—)$_x$CH$_3$ or —(CH$_2$—)$_y$ONO$_2$ R° is hydrogen, —(CH$_2$—)$_m$CH$_3$ or —(CH$_2$—)$_y$ONO$_2$, provided that one R° (and only one) is other than hydrogen, that the sum of n and m does not exceed 7 and that the sum of n and y does not exceed 8, or R and R$_1$ together with the 4- amino nitrogen attached to the furo[3,2-c]pyridine ring form

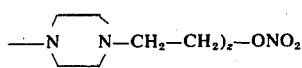

x is 0 or 1,
n is 1 to 7, preferably 3 to 6,
m is 0 to 4,
y is 1 to 4, and
z is 1 to 4, or a pharmaceutically acceptable non-toxic acid addition salt thereof.

A preferred method for preparation of the compounds of formula I involves in a Step A reaction the nitration of the corresponding hydroxy compounds of formula II:

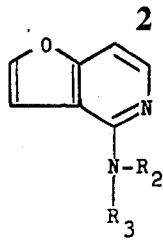
II wherein R$_2$ and R$_3$ are the non-nitrate bearing hydroxyalkyl substituents corresponding to R and R$_1$, respectively, i.e.

R$_2$ is from the group of:
a. —CH$_2$(—CH$_2$)$_n$—OH b) —CH$_2$(—ĊH)$_n$—OH, with R$_a$° substituent c) ĊH(—CH$_2$)$_n$—OH with R$_a$' substituent d. —CH$_2$(—CH$_2$)$_z$—N[—CH$_2$(—CH$_2$)$_y$—OH]$_2$ R$_3$ is from the group of:
e. —CH$_2$(—CH$_2$)$_n$—OH when R$_2$ is (a) as above defined,
f. hydrogen or lower alkyl of 1 to 4 carbon atoms, R$_a$' is —(CH$_2$—)$_x$CH$_3$ or —(CH$_2$—)$_y$OH R$_2$° is hydrogen, —(CH$_2$—)$_m$CH$_3$ or —(CH$_2$—)$_y$OH, provided that one R$_a$° is other than hydrogen, that the sum of n and m does not exceed 7 and that the sum of n and y does not exceed 8, or R$_2$ and R$_3$ together with the 4-amino nitrogen attached to the furo[3,2-c]pyridine ring form

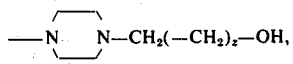

and n, m y and z are as defined.

The preparation of compounds I by step A involves a nitration reaction which may be carried out in a manner known per se for nitrating hydroxyalkyl groups. A preferred method of conducting the nitration involves the reaction of a compound II with nitric acid in presence of a carboxylic acid anhydride which is preferably of from 3 to 8 carbon atoms, more preferably acetic acid anhydride. The reaction may be suitably carried out in an organic solvent medium at temperatures in the range of from minus 70°C. to plus 50°C., preferably minus 5°C. to plus 20°C. The solvent medium for the reaction is preferably provided by employing a lower aliphatic carboxylic acid, e.g. acetic acid, although other well known organic solvents may be employed or the reaction may be carried out employing an excess of the carboxylic acid anhydride. The product compound I may be isolated from the reaction mixture of Step A by working up by established procedures.

A preferred method for preparation of compounds II involves a Step B reaction of a 4-halo-furo[3,2-c]pyridine of formula III:

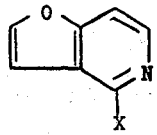
III wherein X is halo from the group of chloro or bromo, preferably chloro, with a compound of formula IV:

wherein $R_2$ and $R_3$ are as defined.

The reaction of Step B is of known type and may be carried out in a conventional manner by subjecting a Compound III to reaction with the compound IV at elevated temperatures which may be suitably in the range of 30°C. to 180°C., preferably 60°C. to 160°C. The reaction may be suitably carried out in an inert organic solvent which may be any of several of the well-known conventional solvents, preferably an aromatic solvent such as benzene. Another preferred solvent is isopropanol. Alternately, the reaction may be initiated and/or carried out in the liquid medium provided by employing an excess of compounds IV when the compound is liquid at the reaction temperature or by fusion of solid reactants. An acid binding agent such as sodium carbonate may be also employed to advantage in the reaction, if desired. The reaction product compound II may be isolated from the reaction mixture of Step B by established procedures.

The compounds of formulae III and IV are either known or may be prepared from know materials by established procedures. Compounds III are known, for example, from Eloy et al., J. Heterocycl. Chem. 1971, 8(1), 57–60 (Fr.).

Also within the scope of the novel compounds of the invention are pharmaceutically acceptable salts not materially affecting the pharmacological effect of the compounds of formula I and formula II. Such salts include the acid addition salts, e.g., the methane sulfonate, hydronitrate, hydrosulfate, fumarate, hydrochloride and maleate. It is convenient to prepare the compounds of formula I as a hydronitrate addition salt. Such salts may be then readily converted to the free bases by conventional procedures. In preparing the free bases of the formula I from the acid addition salts, it is also convenient to employ a buffer system, e.g., a system comprising a 1:1 molar mixture of acetic acid and sodium acetate, followed by working up by conventional procedures. The free bases may be readily converted into the hydronitrate and other acid addition salts by established procedures. The compounds II may be also prepared as acid addition salts and converted to free base form, and vice versa by conventional procedures.

The compounds of formulae I and II and their pharmaceutically acceptable acid addition salts are useful because they possess pharmacological activity in animals. In particular, the compounds are useful as antianginal agents as indicated on intravenous administration (0.5 to 20 milligrams per kilogram) to the anesthetized dog and measurement of blood flow through the anterior descending branch of the left coronary artery.

For the above use, the compounds of the formulae I and II may be combined with a pharmaceutically acceptable carrier, and such other conventional adjuvants as may be necessary, and administered orally in such forms as tablets, capsules, elixirs, suspensions and the like or parenterally in the form of an injectable solution or suspension. For the above-mentioned use, the dosage administered will, of course, vary depending upon the compound used, the therapy desired and the mode of administration. However, satisfactory results are obtained when administered at daily dosage of from about 0.15 milligram to about 75 milligrams per kilogram of body weight, preferably given orally as required or in divided doses 2 to 4 times a day, or in sustained release form. For most larger mammals a dosage of from 16 to 1000 milligrams, pro re nata, provides satisfactory results. The compounds may also be used prophylactically in mammals to prevent or minimize angina attacks at a daily dosage of 16 to 1000 milligrams, or in divided doses of from 4 to 500 milligrams.

Certain compounds of the formula II are also useful as agents in the treatment of myocardial shock (positive inotropic effect) as indicated on intravenous administration (0.5 to 20 milligrams per kilogram) to the anesthetized dog and measuring the myocardial contractile force with a Walton Brodie strain gauge. The compounds of the formula II useful in the treatment of shock include those of the formula IIa:

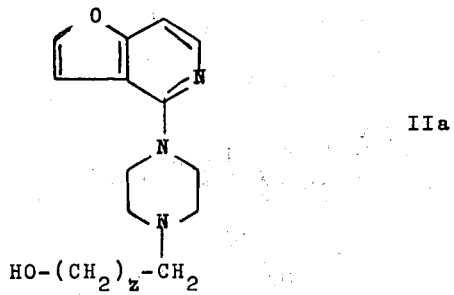

wherein Z is as above defined. A preferred compound for use in the treatment of shock is 4-[4-(2-hydroxyethyl)-1-piperazinyl]-furo[3,2-c]pyridine.

The compounds useful in the treatment of myocardial shock may be administered for such purpose either orally or parenterally, preferably parenterally. The dosage administered for such use will vary of course depending upon the compound used, mode of administration and other known factors. However, in general, satisfactory results are obtained when administered at a dosage of from 0.01 to 200 milligrams per kilogram of body weight administered either daily or pro re nata with the lower range dosages of from 0.01 to 20 mg./kg. applicable to intravenous administration and the dosages of from 0.5 to 200 mg./kg. applicable to oral administration. For most large mammals the administration of from 0.5 to 100 milligrams intravenously pro re nata provides satisfactory results.

For the above usages, oral administration with carriers may take place in such conventional forms as tablets, dispersible powders, granules, capsules, syrups and elixirs. Such compositions may be prepared according to any method known in the art for the manufacture of pharmaceutical compositions, and such compositions may contain one or more conventional adjuvants, such as sweetening agents, flavoring agents, coloring agents and preserving agents, inert diluents, granulating and disintegrating agents, binding agents, lubricating agents and the like. Parental administration may take place in conventional forms such as sterile solutions and suspensions which also may be prepared by conventional techniques. In general, the compositions of the invention adapted for either oral or parental administration may contain 1% to 90% by weight of the active ingredient in combination with the inert carrier, more usually 3% to 40%. Except for the use in the treatment of shocks the preferred pharmaceutical compositions from the standpoint of preparation and ease of administration are solid compositions, particularly hard-filled capsules and tablets.

A representative formulation is a capsule for oral administration 2 to 4 times a day to prevent or lessen the severity of anginal attacks and prepared by standard capsulating techniques to contain:

| Capsule Ingredients | Weight (mg) |
|---|---|
| Compound of Step B of Example 1 | 50 |
| Lactose | 300 |

Compositions for parenteral administration for use, for example, in the treatment of shock, may be formulated by well-known methods to contain an effective amount of a compound I or II as active ingredient in a conventional inert carrier or suspension or solvent medium, together with other additives such as dispersing agents, wetting agents, buffering agents and other conventional ingredients, as desired.

A representative formulation for intravenous administration for treatment of shock (pro re nata) is a solution prepared by standard procedures and containing the following ingredients:

| Ingredient | Weight (%) |
|---|---|
| Compound of Step A of Example 1 | 5 (10 milligrams) |
| Sodium chloride | to make isotonic |
| Buffer Agent | to adjust pH |
| Ethanol, U.S.P. | 10–20 |
| Propylene Glycol | 15–25 |
| Water for Injection | 55–75 |

The following examples are given for the purpose of illustration only.

EXAMPLE 1

4-[4-(2-hydroxyethyl)-1-piperazino]-furo[3,2-c]pyridine and nitrate

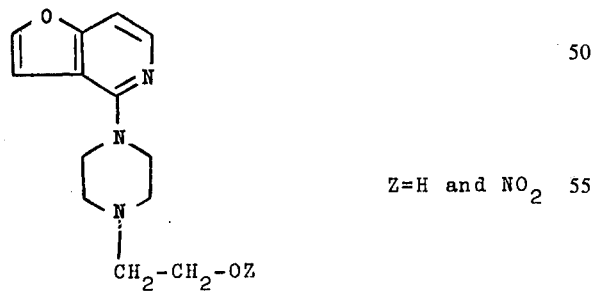

Z=H and $NO_2$

Step A: Preparation of 4-[4-(2-hydroxyethyl)-1-piperazino]-furo[3,2-c]pyridine in dihydrochloride salt form A mixture of 3.5 g. of 4-chloro-furo[3,2-c] pyridine, 3.0 g. of sodium carbonate and 3.0 g. of 2-hydroxyethylpiperazine is heated at 140° for 10 hours. The reaction mixture is distributed between chloroform and water, the chloroform extract is dried, evaporated in vacuo. The residue is dissolved in ethanol saturated with hydrogen chloride. The resulting crystals are recovered by filtering, washed with ethanol, then with diethyl ether, dissolved in water and crystallized by adding ethanol. After filtering, the crystals are dried under high vacuum to obtain 4-[4-(2-hydroxyethyl)-1-piperazino]-furo[3,2-c]pyridine dihydrochloride, m.p. 282°C. (decomp.).

Step B: Preparation of 4-[4-(2-hydroxyethyl)-1-piperazino]-furo[3,2-c]pyridine nitrate.

A solution of about 1.0 g. of 4-[4-(2-hydroxyethyl)-1-piperazino]furo[3,2-c]pyridine in 2.0 ml. of glacial acetic acid is added dropwise to a stirred mixture of 5.1 ml. of acetic anhydride and 1.7 ml. of 90% nitric acid at a temperature of minus 2°C. to 0°C. The resulting mixture is stirred for 1 hour and then added to an excess of ice-cold aqueous ammonia solution. The resulting mixture is extracted with methylene chloride, dried and evaporated to a dark orange oil which is chromatographed over silica gel eluting with 50% chlorofrom in methylene chloride. The eluate is evaporated in vacuo to an oil which is dissolved in ethanol and treated with hydrogen chloride saturated ethanol. Diethyl ether is added and the resulting crystals are filtered off and washed with diethyl ether to obtain 4-[4-(2-hydroxyethyl)-1-piperazino]-furo[3,2-c]pyridine nitrate, m.p. 155°C. (decomp.), in dihydrochloride form.

EXAMPLE 2

Following the procedure of Example 1, the following compounds are prepared:
A-1. 4-(5-hydroxypentyl)amino-furo[3,2-c]pyridine.
A-2. 4-(5-hydroxypentyl)amino-furo[3,2-c]pyridine nitrate.
B-1. 4-(2,3-dihydroxypropyl)amino-furo[3,2-c] pyridine.
B-2. 4-(2,3-dihydroxypropyl)amino-furo[3,2-c] pyridine dinitrate.
C-1. 4-[3-bis(2-hydroxyethyl)aminopropyl]amino-furo[3,2-c]pyridine.
C-2. 4-[3-bis(2-hydroxyethyl)aminopropyl]amino-furo[3,2-c]pyridine dinitrate.
D-1. 4-(N-methyl-N-4-hydroxybutyl)amino-furo[3,2-c]pyridine.
D-2. 4-(N-methyl-N-4-hydroxybutyl)amino-furo[3,2-c]pyridine nitrate.
E-1. 4-di(3-hydroxypropyl)amino-furo[3,2-c] pyridine.
E-2. 4-di(3-hydroxypropyl)amino-furo[3,2-c] pyridine dinitrate.

What is claimed is:
1. A compound of the formula:

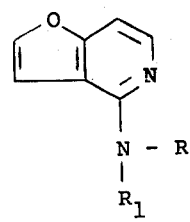

wherein
R is from the group of:
  a. $-CH_2(-CH_2)_n-ONO_2$ b) $-CH_2(-CH)_n-ONO_2$ with $R°$ above c) $-CH(-CH_2)_n-ONO_2$ with $R'$ above d. $-CH_2(-CH_2)_z-N[-CH_2(-CH_2)_y-ONO_2]_2$ $R_1$ is from the group of:

e. $-CH_2(-CH_2)_n-ONO_2$ when R is a) as above defined, f. hydrogen or alkyl of 1 to 4 carbon atoms, $R'$ is $-(CH_2-)_xCH_3$ or $-(CH_2-)_yONO_2$, $R°$ is hydrogen, $-(CH_2-)_mCH_3$ or $-(CH_2-)_yONO_2$, provided that one $R°$ is other than hydrogen, that the sum of $n$ and $m$ does not exceed 7 and the sum of $n$ and $y$ does not exceed 8, $n$ is 1 to 7,
$m$ is 0 to 4,
$x$ is 0 to 1,
$y$ is 1 to 4, and
$z$ is 1 to 4, or a pharmaceutically acceptable acid addition salt thereof.

2. A compound of claim 1 in which $R_1$ is hydrogen.

3. A compound of claim 2 in which R is $-CH_2(-CH_2)_n-ONO_2$.

4. The compound of claim 3 in which $n$ is 4.

5. A compound of claim 2 in which R is $-CH_2(-CH_2)_z-N[-CH_2(CH_2)_y-ONO_2]_2$.

6. The compound of claim 5 in which $y$ is 1 and $z$ is 2.

7. A compound of the formula:

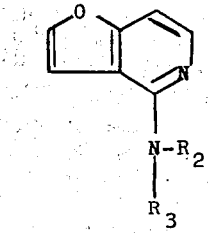

wherein $R_2$ is from the group of:

a. $-CH_2(-CH_2)_n-OH$ b) $-CH_2(-CH)_n-OH$ with $R_a°$ above c) $-CH(-CH_2)_n-OH$ with $R_a'$ above d. $-CH_2(-CH_2)_z-N[-CH_2(-CH_2)_y-OH]_2$ $R_3$ is from the group of:

e. $-CH_2(-CH_2)_n-OH$ when $R_2$ is (a) as above defined f. hydrogen or alkyl of 1 to 4 carbon atoms $R_a'$ is $-(CH_2-)_xCH_3$ or $-(CH_2-)_yOH$ $R_a°$ is hydrogen, $-(CH_2-)_mCH_3$ or $(CH_2-)_yOH$, provided that one $R°$ is other than hydrogen, that the sum of $n$ and $m$ does not exceed 7 and the sum of $n$ and $y$ does not exceed 8, and $n, m, x, y$ and $z$ are as defined in claim 1, or a pharmaceutically acceptable acid addition salt thereof.

8. A compound of claim 7 in which $R_3$ is hydrogen.

9. A compound of claim 8 in which $R_2$ is $-CH_2(-CH_2)_n-OH$.

10. The compound of claim 9 in which $n$ is 4.

11. A compound of claim 8 in which $R_2$ is $-CH_2(-CH_2)_z-N[-CH_2(-CH_2)_y-OH]_2$.

12. The compound of claim 11 in which $y$ is 1 and $z$ is 2.

* * * * *